United States Patent [19]

Brahm et al.

[11] Patent Number: 5,798,431
[45] Date of Patent: Aug. 25, 1998

[54] PROCESS FOR THE PRODUCTION OF POLYISOCYANATES CONTAINING ISOCYANURATE GROUPS FROM ALIPHATIC AND AROMATIC ISOCYANATE COMPOUNDS

[75] Inventors: Martin Brahm, Leverkusen; Carl-gerd Dieris, Dormagen; Lutz Schmalstieg, Köln; Reinhard Halpaap, Odenthal, all of Germany

[73] Assignee: Bayer Aktiengesellschaft, Leverkusen, Germany

[21] Appl. No.: 679,888

[22] Filed: Jul. 15, 1996

[30] Foreign Application Priority Data

Jul. 24, 1995 [DE] Germany ............... 195 26 920.9

[51] Int. Cl.$^6$ .................. C08G 18/79; C07D 251/34
[52] U.S. Cl. .................. 528/73; 528/52; 528/67; 544/193; 544/221; 544/222
[58] Field of Search .................. 544/193, 221, 544/222; 528/52, 67, 73

[56] References Cited

U.S. PATENT DOCUMENTS

| | | | |
|---|---|---|---|
| 4,115,373 | 9/1978 | Henes et al. | 528/48 |
| 4,412,073 | 10/1983 | Robin | 544/193 |
| 4,518,761 | 5/1985 | Richter et al. | 528/67 |
| 4,537,961 | 8/1985 | Robin | 544/193 |
| 4,552,946 | 11/1985 | Scholl et al. | 528/67 |
| 4,675,401 | 6/1987 | Robin | 544/193 |
| 4,697,014 | 9/1987 | Robin | 544/193 |
| 5,159,045 | 10/1992 | Haseyama et al. | 528/45 |
| 5,208,334 | 5/1993 | Potter et al. | 544/193 |
| 5,496,642 | 3/1996 | Martinez et al. | 428/423.1 |

FOREIGN PATENT DOCUMENTS

| | | |
|---|---|---|
| 2616415 | 11/1977 | Germany . |
| 1244416 | 9/1971 | United Kingdom . |

OTHER PUBLICATIONS

J. prakt. Chem., 336, 185–200 1994.

*Primary Examiner*—Rabon Sergent
*Attorney, Agent, or Firm*—Joseph C. Gil; Thomas W. Roy

[57] ABSTRACT

A process for the production of polyisocyanates containing isocyanurate groups by the catalytic trimerization of a mixture of low molecular weight isocyanate components having aliphatically and aromatically bound isocyanate groups in the presence of aminosilyl compounds, the resulting polyisocyanates and their use in coating compositions.

20 Claims, No Drawings

PROCESS FOR THE PRODUCTION OF POLYISOCYANATES CONTAINING ISOCYANURATE GROUPS FROM ALIPHATIC AND AROMATIC ISOCYANATE COMPOUNDS

BACKGROUND OF THE INVENTION

1. Field of the Invention

The present invention relates to a process for the production of polyisocyanates containing isocyanurate groups by the catalytic trimerization of a mixture of isocyanate components having aliphatically and aromatically bound isocyanate groups in the presence of amino silyl compounds, and to the their use in coating compositions.

2. Description of the Prior Art

Catalytic trimerization of isocyanate groups is a well known modification reaction for diisocyanates to produce coating compositions with outstanding properties. A distinction is drawn in this connection between trimerization products prepared from aliphatic isocyanates components and those prepared from aromatic isocyanates.

Coatings based on lacquer polyisocyanates prepared from aliphatic diisocyanates exhibit excellent light stability and chemical resistance and are used, for example, in automotive lacquer coatings. Such isocyanurate-based polyisocyanates are known (see, for example, *J. prakt. Chem.*, 336, 185–200 (1994)). Catalysts used for the trimerization of aliphatic diisocyanates are preferably alkyl(aryl)-ammonium hydroxides, alkoxides, amines and amino silyl compounds.

In contrast, lacquer polyisocyanates produced from aromatic isocyanates are highly reactive and thus are used as fast drying and hardening crosslinking agents. Mannich bases are preferably used as trimerization catalysts for these polyisocyanates as described in, e.g. DE-A 2,551,534).

Co-trimerization products based upon aliphatic and aromatic diisocyanates synergistically combine the properties of purely aliphatic and purely aromatic analogs and are preferably used where there is a requirement for relatively light-fast and hard coatings in conjunction with rapid curing. However, co-trimerization of highly reactive aromatic diisocyanates with much less reactive aliphatic diisocyanates is difficult to perform.

Only alkylphosphanes, such as tributylphosphane, have been described as suitable catalysts for co-trimerization (DE-A 1,954,093). Disadvantages in this case are, however, the poor handling properties of the sometimes pyrophoric phosphanes, catalyst deactivation, etc..

Another process for the production of co-trimerization products is known from DE-A 3,144,672. In this case, co-trimerization with alkali metal salts may only be achieved by slowly adding the highly reactive aromatic compounds to a mixture of aliphatic compounds and catalyst. This produces an uncontrolled reaction of aromatic and aliphatic diisocyanates together and not true co-trimerization.

It is known to use aminosilyl compounds for the production of lacquer polyisocyanates, for example, from U.S. Pat. No. 4,412,073, 4,537,961, 4,675,401 and 4,697,014, and EP-A 57,653, 89,297 and 187,105. The catalytic trimerization of aliphatic or aromatic diisocyanates is described, but not the trimerization of mixtures of aliphatic and aromatic isocyanates.

It is an object of the present invention to prepare polyisocyanates having isocyanurate groups and a low monomer content and containing both aromatic and aliphatic isocyanate compounds.

This object may be achieved in accordance with the present invention by reacting a mixture of aliphatic and aromatic isocyanates in the presence of aminosilyl compounds as catalysts to produce isocyanates containing both aromatic and aliphatic isocyanate compounds.

A particularly surprising feature of the present invention is that the less reactive aliphatic isocyanates are preferentially incorporated into the isocyanurate. This may be confirmed by determining the residual monomer content directly after trimerization.

SUMMARY OF THE INVENTION

The present invention relates to a process for the production of isocyanurate group-containing polyisocyanates by catalytically trimerizing a mixture of a) 10 to 90 parts of a low molecular weight isocyanate component A) having aliphatically bound isocyanate groups, an average molecular weight of 128 to 800 and an average NCO functionality of 1.7 to 2.2 and b) 10 to 90 parts of a low molecular weight isocyanate component B) having aromatically bound isocyanate groups, an average molecular weight of 148 to 800 and an average NCO functionality of 1.7 to 2.2, in the presence of 0.1 to 10 parts of an aminosilyl compound C) per 100 parts of isocyanate components A) and B) and subsequently removing excess, distillable isocyanate components A) and B) to obtain polyisocyanates having a monomer content of less than 0.7%, based on the weight of polyisocyanate solids.

The present invention also relates to the resulting products and to their use for the production of coatings.

DETAILED DESCRIPTION OF THE INVENTION

Isocyanate component A) is selected from compounds having aliphatic and/or cycloaliphatic isocyanate groups, an average molecular weight of 128 to 800, preferably of 128 to 300 and an NCO functionality of 1.7 to 2.3, preferably 1.9 to 2.1 and more preferably 2. The NCO content of component A) is 30 to 60%, preferably 32 to 50%, by weight.

Suitable diisocyanates include 1,4-diisocyanatobutane, 1,5-diisocyanatopentane, 1,6-diisocyanatohexane, 1,11-diisocyanatoundecane, dodecamethylene diisocyanate, 2,2, 4- and 2,4,4-trimethyl-1,6-diisocyanatohexane, 1-isocyanato-3-isocyanatomethyl-3,5,5-trimethyl-cyclohexane (isophorone diisocyanate), 1,3-diisocyanato-cyclobutane, 1,3- and 1,4-diisocyanatocyclo-hexane, 4,4'-bis-(isocyanatocyclohexyl)-methane, 1,2-bis-(isocyanatomethyl)cyclobutane, 1,3- and 1,4-bis-(isocyanatomethyl)cyclohexane, hexahydro-2,4- and/or - 2,6-diisocyanatotoluene, bis-isocyanatomethyl-norbornane (isomeric mixture), 2,5- and 2,6-bis-(isocyanatomethyl)-bicyclo[2.2.1.]nheptane, lysine diisocyanate, 1isocyanato-4 (3)-isocyanatomethyl-1-metholcyclohexane, p-xylyene diisocyanate, 2,3-bis-(8-isocyanato-octyl)-4-octyl-5-hexylcyclohexane or any desired mixtures.

For modification purposes, it is also possible to use mono-isocyanates, such as butyl isocyanate, hexyl isocyanate, 2-ethylhexyl isocyanate, stearyl isocyanate and cyclohexyl isocyanate, mixed with diisocyanates. Higher functional isocyanate compounds may also be used, provided that the total functionality of component A) is not greater than 2.3, preferably 2.1. The stated mono- and diisocyanates may be modified by urethane, allophanate, urea, biuret, uretidione and/or carbodiimide groups.

1,6-diisocyanatohexane is preferably used as isocyanate component A).

Isocyanate component A) is selected from compounds having aromatically bound isocyanate groups, an average molecular weight of 148 to 800, preferably 148 to 250 and an NCO functionality of 1.7 to 2.3, preferably 1.9 to 2.1 and more preferably 2.

Suitable compounds include the isomeric diisocyanatodiphenyl-methanes, 2,4- and/or 2,6-tolylene diisocyanate, 1,3-phenylene diisocyanate, 1,4-phenylene diisocyanate, 4,4'-diphenylene diisocyanate, 1,5-diisocyanate, 1,4-naphthylene diisocyanate, 4,4'-diisocyanatodiphenyl ether and mixtures thereof.

Monoisocyanates such as phenyl isocyanate and the toluyl isocyanates may also be used in blends with more highly functional and/or difunctional isocyanate compounds. Isocyanate component B) may also be modified by urethane, allophanate, urea, biuret, uretidione and/or carbodiimide groups.

2,4- and/or 2,6-tolylene diisocyanate is preferably used as isocyanate component B).

Isocyanate component A) is used in an amount of 10 to 90, preferably 20 to 70 and more preferably 30 to 60 parts, per 100 parts of isocyanate components A) and B).

Aminosilyl compounds C) are selected from compounds, which have one or more Si-N groups and correspond to the following formula

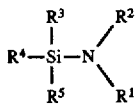

wherein
- $R^1$ represents hydrogen or a saturated or unsaturated $C_6$–$C_{22}$ aliphatic, $C_5$–$C_{20}$ cycloaliphatic or $C_6$–$C_{24}$ aromatic hydrocarbons optionally substituted with Cl or Br,
- $R^2$ represents a saturated or unsaturated $C_1$–$C_{22}$ aliphatic, $C_5$–$C_{20}$ cycloaliphatic or $C_6$–$C_{24}$ aromatic hydrocarbons optionally substituted with Cl or Br or represents the group $SiR^3R^4R^5$ group, provided that $R^1$ and $R^2$ may also form a heterocyclic ring having 2 to 6 carbon atoms in which carbon atoms present in the ring may be replaced by heteroatoms such as oxygen, sulphur, phosphorus or nitrogen and
- $R^3$, $R^4$ and $R^5$ are the same or different and represent saturated or unsaturated $C_1$-$C_{22}$ aliphatic, $C_5$-$C_{20}$ cycloaliphatic or $C_6$-$C_{24}$ aromatic hydrocarbons optionally substituted with Cl or Br.

Preferably $R^3$, $R^4$ and $R^5$ are the same or different and represent methyl, ethyl, propyl or butyl groups, or the isomers thereof. More preferably these radicals represent methyl groups.

Suitable aminosilyl compounds (I) are commercially available products. Preferred catalysts include compounds include hexamethyl-disilazane and N-(bis)silylated morpholine, piperidine and piperazine.

Catalysts C) are preferably used in concentrations of 0.1 to 10 parts, more preferably 0.8 to 5 parts, per 100 parts of component A and B. In order to facilitate handling, the catalysts may optionally also be used in dissolved form.

Catalytic trimerization is performed at a temperature of approximately 50° to 140° C., preferably 80° to 125° C. After completion of the trimerization reaction, the catalyst may optionally be deactivated by adding a catalyst poison.

Suitable catalyst poisons are preferably monofunctional or polyfunctional alcohols or mercaptans, more preferably carboxylic acids.

After the trimerization reaction and optional termination with deactivators or catalyst poisons, excess, distillable monomeric isocyanates A and B are removed from the reaction mixture, preferably by film distillation under vacuum. The total residual content of distillable monomeric isocyanates A and B in the final product is less than 0.7%, preferably less than 0.5% and more preferably less than 0.1%.

Solvents may then be added to the resulting products in an amount sufficient to provide a solids content of at least 40 wt.%, preferably at least 60 wt.%. Suitable solvents include toluene, xylene, cyclohexane, chlorobenzene, butyl acetate, ethyl acetate, ethylene glycol monoethyl ether acetate, pentyl acetate, hexyl acetate, methoxypropyl acetate, tetrahydrofuran, dioxane, acetone, methyl ethyl ketone, mineral spirits, highly substituted commercial available aromatic solvents (such as Solvent Naphtha, Solvesso, Shellsol, Isopar, Nappar and Diasol solvents), heavy benzole, tetralin, decalin, alkanes having more than 6 carbon atoms and mixtures of these solvents.

In general the polyisocyanates produced by the process according to the invention are colorless, storage-stable coating materials which may be cured under the action of atmospheric moisture alone.

They are preferably used as crosslinking agents in two-component compositions in combination with known isocyanate-reactive compounds. Examples of these co-reactants include hydroxy-functional polyethers, polyesters, polyamides, polycarbonates, polyacrylates, polybutadienes and copolymer grades of the stated hydroxy-functional polymers, low molecular weight di- and polyols, dimeric and trimeric fatty alcohols and amino-functional compounds.

One-component compositions may also be formulated with blocked isocyanate-reactive compounds. The products produced using the process according to the invention may also be used in blocked form either in combination with or in the absence of a co-reactant. Curing is carried put at elevated temperatures of up to approximately 200° C.

In addition to the products according to the invention, the coating compositions may also contain other known additives, such as catalysts, wetting agents, levelling agents, anti-skinning agents, anti-foaming agents, solvents, flatting agents (such as silica, aluminum silicates and high-boiling waxes), viscosity regulators, pigments, dyes, UV absorbers, and stabilizers against thermal and/or oxidative degradation.

The resultant coating compositions may be used for coating any desired substrates such as wood, plastics, leather, paper, textiles, glass, ceramics, plaster, masonry, metals and concrete. They may be applied using conventional methods, such as spraying, brushing, flow coating, dipping and rolling. The coating compositions may be used both as clear lacquers and as pigmented lacquers.

The coatings produced from the products according to the invention cure at room temperature (approx. 20° C.) within a few minutes to several hours to yield high quality, hard coatings. Curing may also proceed at lower temperatures (down to −5° C.) or be accelerated at higher temperatures (80° to 200° C.).

EXAMPLES

All stated parts and percentages are by weight unless otherwise indicated.

Example 1

608 g (3.5 mol) of 2,4-tolylene diisocyanate and 391 g (2.3 mol) of 1,6-hexamethylene diisocyanate were initially introduced into a stirred apparatus consisting of a flat ground flask, internal thermometer, metal stirrer, dropping funnel and reflux condenser with a drying tube attachment and heated to 110° C. under a nitrogen atmosphere. 15 g (1.5%) of hexamethyldisilazane were then added dropwise to this solution and the mixture was stirred at a temperature of 115° C. Untie an NCO content of 39% was reached (approximately 8 hours). The reaction mixture was cooled and excess monomer was removed by film distillation (temperature 180° C., 0.5 mbar). A 60% solution of the resultant solid resin in butyl acetate exhibited the following characteristics:

NCO content: 11.4%
Solids content: 60%
Viscosity: approx. 500 mPa·s
Free HDI: 0.15%
Free TDI: 0.18%
TDI/HDI molar ratio in product: 1.2

Example 2

Example 1 was repeated with the exception that 15 g of N-trimethyl-silylmorpholine was used as the catalyst. An NCO content of 38.5% was reached after 6 hours, at which time the reaction was terminated by adding 10.4 g of butanol at 50° C. After separation of excess monomer and dissolution in butyl acetate, a virtually colorless product having the following characteristics was obtained:

Titrated NCO content: 11.0%
Solids content: 60%
Viscosity: approx. 600 mPa·s
Free HDI: 0.1%
Free TDI: 0.2%
IHDI Molar ratio in product: 1.3

Example 3 (Comparison)

Example 1 was repeated with the exception that 1.3 g of a Mannich base based on phenol/dimethylamine, 40% in butyl acetate, was used as the catalyst. The reaction was terminated at an NCO content of 38% by adding 0.3 g of benzoyl chloride. Direct analysis of the free monomer content revealed that TDI had virtually exclusively been incorporated into the isocyanurate. The free HDI content was virtually unchanged in comparison with its content in the starting mixture.

4. Comparative example (not according to the invention)

Example 1 was repeated with the exception that 20 g (2% relative to total batch) of N,N'-bis-(trimethylsilyl)-N,N'-dibutylurea was used as the catalyst. Even after 12 hours' reaction, the NCO content of the solution had fallen only slightly to 41.5%. Target value (see example 1): approx. 38%. This type of catalyst was thus incapable of performing cotrimerization of hexamethylene diisocyanate and tolylene diisocyanate.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of an isocyanurate group-containing polyisocyanate which comprises catalytically trimerizing a mixture of a) 10 to 90 parts by weight of a low molecular weight isocyanate component A) having aliphatically and/or cycloaliphatically bound isocyanate groups, an average molecular weight of 128 to 800 and an average NCO functionality of 1.7 to 2.2 and b) 10 to 90 parts by weight of a low molecular weight isocyanate component B) having aromatically bound isocyanate groups, an average molecular weight of 148 to 800 and an average NCO functionality of 1.7 to 2.2, in the presence of 0.1 to 10 parts by weight, per 100 parts by weight of isocyanate components A) and B), of an aminosilyl compound C) corresponding to the formula

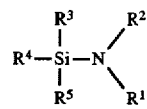

wherein $R^1$ represents hydrogen or a saturated or unsaturated $C_1$–$C22$ aliphatic, $C_5$–$C_{20}$cycloaliphatic or $C_6$–$C_{24}$ aromatic hydrocarbons optionally substituted with Cl or Br, $R^2$ represents a saturated or unsaturated $C_1$–$C_{22}$ aliphatic, $C_5$–$C_{20}$ cycloaliphatic or $C_6$–$C_{24}$ aromatic hydrocarbons optionally substituted with Cl or Br or represents the group $SiR^3R^4R^5$ group, provided that $R^1$ and $R^2$ may also form a heterocyclic ring having 2 to 6 carbon atoms in which carbon atoms present in the ring may be replaced by heteroatoms and $R^3$, $R^4$ and $R^5$ are the same or different and represent saturated or unsaturated $C_1$–$C_{22}$ aliphatic, $C_1$–$C_{20}$ cycloaliphatic or $C_6$–$C_{24}$, aromatic hydrocarbons optionally substituted with Cl or Br, and subsequently removing excess, distillable isocyanate components A) and B) to obtain a polyisocyanate having a monomer content of less than 0.7%, based on the weight of polyisocyanate solids.

2. The process of claim 1 in which isocyanate components A) and B) are diisocyanates.

3. The process of claim 1 wherein isocyanate component A) comprises 1,6-diisocyanatohexane and isocyanate component B) comprises 2,4- and/or 2,6-tolylene diisocyanate.

4. The process of claim 1 wherein isocyanate component A) is present in an amount of 20 to 70 parts by weight and isocyanate component B) is present in an amount of 30 to 80 parts by weight.

5. The process of claim 2 wherein isocyanate component A) is present in an amount of 20 to 70 parts by weight and isocyanate component B) is present in an amount of 30 to 80 parts by weight.

6. The process of claim 3 wherein isocyanate component A) is present in an amount of 20 to 70 parts by weight and isocyanate component B) is present in an amount of 30 to 80 parts by weight.

7. The process of claim 1 wherein 0.8 to 5 parts by weight of an aminosilyl compound C) are present per 100 parts by weight of isocyanate components A) and B).

8. The process of claim 1 wherein catalyst C) comprises an N-silylated heterocyclic.

9. The process of claim 2 wherein catalyst C) comprises an N-silylated heterocyclic.

10. The process of claim 6 wherein catalyst C) comprises an N-silylated heterocyclic.

11. The process of claim 1 wherein catalyst C) comprises an N-silylated cyclic amine containing at least one heteroatom in the ring in addition to nitrogen.

12. The process of claim 2 wherein catalyst C) comprises an N-silylated cyclic amine containing at least one heteroatom in the ring in addition to nitrogen.

13. The process of claim 6 wherein catalyst C) comprises an N-silylated cyclic amine containing at least one heteroatom in the ring in addition to nitrogen.

14. An isocyanurate group-containing polyisocyanate which is prepared by a process comprising catalytically trimerizing a mixture of
   a) 10 to 90 parts by weight of a low molecular weight isocyanate component A) having aliphatically and/or cycloaliphatically bound isocyanate groups, an average molecular weight of 128 to 800 and an average NCO functionality of 1.7 to 2.2 and
   b) 10 to 90 parts by weight of a low molecular weight isocyanate component B) having aromatically bound isocyanate groups, an average molecular weight of 148 to 800 and an average NCO functionality of 1.7 to 2.2,
in the presence of 0.1 to 10 parts by weight, per 100 parts by weight of isocyanate components A) and B), of an aminosilyl compound C) corresponding to the formula

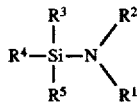

wherein
   $R^1$ represents hydrogen or a saturated or unsaturated $C_1$–$C_{22}$ aliphatic, $C_5$–$C_{20}$ cycloaliphatic or $C_6$–$C_{24}$ aromatic hydrocarbons optionally substituted with Cl or Br,
   $R^2$ represents a saturated or unsaturated $C_1$–$C_{22}$ aliphatic, $C_5$–$C_{20}$ cycloaliphatic or $C_6$–$C_{24}$ aromatic hydrocarbons optionally substituted with Cl or Br or represents the group $SiR^3R^4R^5$ group, provided that $R^1$ and $R^2$ may also form a heterocyclic ring having 2 to 6 carbon atoms in which carbon atoms present in the ring may be replaced by heteroatoms and
   $R^3$, $R^4$ and $R^5$ are the same or different and represent saturated or unsaturated $C_1$–$C22$ aliphatic, $C_5$–$C_{20}$ cycloaliphatic or $C_6$–$C_{24}$ aromatic hydrocarbons optionally substituted with Cl or Br,
and subsequently removing excess, distillable isocyanate components A) and B) to obtain a polyisocyanate having a monomer content of less than 0.7%, based on the weight of polyisocyanate solids.

15. The polyisocyanate of claim 14 in which isocyanate components A) and B) are diisocyanates.

16. The polyisocyanate of claim 14 wherein isocyanate component A) comprises 1,6-diisocyanatohexane and isocyanate component B) comprises 2,4- and/or 2,6-tolylene diisocyanate.

17. The polyisocyanate of claim 14 wherein isocyanate component A) is present in an amount of 20 to 70 parts by weight and isocyanate component B) is present in an amount of 30 to 80 parts by weight.

18. The polyisocyanate of claim 15 wherein isocyanate component A) is present in an amount of 20 to 70 parts by weight and isocyanate component B) is present in an amount of 30 to 80 parts by weight.

19. The polyisocyanate of claim 16 wherein isocyanate component A) is present in an amount of 20 to 70 parts by weight and isocyanate component B) is present in an amount of 30 to 80 parts by weight.

20. A coating composition in which the binder comprises the polyisocyanate of claim 14.

* * * * *